United States Patent
Samain

(10) Patent No.: US 9,265,709 B2
(45) Date of Patent: Feb. 23, 2016

(54) USE OF PEPTIDES AS ANTIDANDRUFF AGENTS

(75) Inventor: Henri Samain, Bievres (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 13/516,397

(22) PCT Filed: Dec. 17, 2010

(86) PCT No.: PCT/EP2010/070169
§ 371 (c)(1),
(2), (4) Date: Jun. 15, 2012

(87) PCT Pub. No.: WO2011/073439
PCT Pub. Date: Jun. 23, 2011

(65) Prior Publication Data
US 2012/0258906 A1    Oct. 11, 2012

Related U.S. Application Data

(60) Provisional application No. 61/290,094, filed on Dec. 24, 2009.

(30) Foreign Application Priority Data

Dec. 17, 2009  (FR) ..................................... 09 59155

(51) Int. Cl.
*A61K 38/00* (2006.01)
*A61P 31/00* (2006.01)
*A61K 38/10* (2006.01)
*A61K 8/64* (2006.01)
*A61Q 5/00* (2006.01)

(52) U.S. Cl.
CPC .. *A61K 8/64* (2013.01); *A61Q 5/006* (2013.01)

(58) Field of Classification Search
None
See application file for complete search history.

(56) References Cited

U.S. PATENT DOCUMENTS

| 5,753,600 | A | 5/1998 | Kamegai et al. |
| 7,371,720 | B2* | 5/2008 | Ribeiro De Paiva et al. .. 514/2.4 |
| 2002/0172648 | A1* | 11/2002 | Hehner et al. ............... 424/70.1 |
| 2004/0242488 | A1 | 12/2004 | Ribeiro De Paiva et al. |

FOREIGN PATENT DOCUMENTS

| DE | 198 41 794 | | 3/2000 |
| DE | 198 41 795 | * | 3/2000 |
| JP | 63 96116 | | 4/1988 |
| JP | 1 68307 | | 3/1989 |

OTHER PUBLICATIONS

Wolf et al, "DE 198 41 795 A1" translation, Mar. 2000.*
Cao et al, Expression and purification of antimicrobial peptide adenoregulin with C-amidated terminus in *Escherichia coli*, Protein Expression and Purification 40 (2005) 404-410.*
Roia et al, Resident Microbial Flora of the Human Scalp and its Relationship to Dandruff, J. Soc. Cosmetic Chemists, 20, 113-134, 1969.*
Nicolas, P., et al., "The dermaseptin superfamily: A gene-based combinatorial library of antimicrobial peptides," Biochimica et Biophysica Acta, vol. 1788, pp. 1537-1550, (2009).
Leite, J.R.S.A., et al., "Phylloseptins: a novel class of anti-bacterial and anti-protozoan peptides from the *Phyllomedusa* genus," Peptides, vol. 26, pp. 565-573, (2005).
International Search Report Issued Mar. 27, 2012 in PCT/EP10/70169 Filed Dec. 17, 2010.
Amram Mor, et al., "Isolation, Amino Acid Sequence, and Synthesis of Dermaseptin, a Novel Antimicrobial Peptide of Amphibian Skin", Biochemistry (1991),30, 8824-8830.
Amram Mor, et al., "The NH$_2$-terminal α-Helical Domain 1-18 of Dermaseptin is Responsible for Antimicrobial Activity", The Journal of Biological Chemistry, vol. 269, No. 3, Jan. 21, 1994, pp. 1934-1939.

* cited by examiner

*Primary Examiner* — Karlheinz R Skowronek
*Assistant Examiner* — Sergio Coffa
(74) *Attorney, Agent, or Firm* — Oblon, McClelland, Maier & Neustadt, L.L.P.

(57) ABSTRACT

The present invention relates to compositions comprising peptides with antidandruff activity. The invention also relates to the use of these peptides as antidandruff agents, or in methods for treating dandruff.

9 Claims, No Drawings

USE OF PEPTIDES AS ANTIDANDRUFF AGENTS

The present invention relates to compositions comprising peptides with antidandruff activity. The invention also relates to the use of these peptides as antidandruff agents, and to a method for treating dandruff.

Desquamative disorders of the hair and/or the scalp such as dandruff or seborrhoeic dermatitis are in particular associated with the permanent presence of a characteristic yeast of the genus *Malassezia* (in particular *ovalis, orbiculare, furfur, globosa* or *restricta*), this genus previously being known as *Pityrosporum* (*ovale* or *orbiculare*).

To combat desquamative disorders of the scalp and in particular dandruff or seborrhoeic dermatitis, it is known practice to use antifungal agents applied topically in various forms. These agents are directed, by means of their antifungal power, towards eliminating or controlling the multiplication of a resident yeast of the scalp, belonging to the genus *Malassezia* and its variants (in particular *M. ovalis, M. orbiculare, M. furfur, M. globosa* or *M. restricta*).

Many agents are claimed, known and used for this purpose, among which mention may be made of zinc pyrithione, omadine, tars, triclosan, piroctone olamine, selenium disulfide and, more recently, tropolone and hinokitiol (Research Disclosure No. 429, January 2000).

The antifungal activity of these substances towards a characteristic yeast of the genus *Malassezia* is not sufficiently satisfactory. Specifically, in many cases, the reduction of dandruff is only moderate despite the regular use of these products. Since these active agents are generally used in high concentrations, it becomes difficult to increase their concentration in order to create products suited to these particular cases. Furthermore, the action of these active agents does not show satisfactory specificity, in the sense that it is not directed only towards the microorganism(s) directly responsible for the development of dandruff. It would therefore be advantageous to have available active agents that are capable of destroying the microorganisms responsible for dandruff, while at the same time being friendly to the microbial balance of the scalp.

U.S. Pat. No. 6,255,279 describes the use of an antimicrobial peptide having the sequence GIGDPVTXLKSGAIXH-PVFXPRRYKQIGGXGLPXTKXXXX, in which X may be any amino acid, for treating dandruff. The use of a specific peptide isolated from human skin is also described.

However, the need remains for novel selective active agents that show activity on the microorganisms responsible for desquamative disorders of the scalp at low concentration. Products whose action is friendlier to the microbial flora of the scalp would also be particularly advantageous.

The Applicant has now discovered, surprisingly and unexpectedly, that these objectives can be achieved by using antimicrobial peptides that will be defined in greater detail hereinbelow.

A first aspect of the invention relates to a composition, preferably a cosmetic composition, comprising, in a physiologically acceptable medium, at least one phylloseptin or dermaseptin antimicrobial peptide, a functional variant or a salt of such a peptide.

The invention is also related to the use of at least one phylloseptin or dermaseptin antimicrobial peptide, a functional variant or a salt of such a peptide, as an agent for combating desquamative disorders of the scalp and more particularly for combating dandruff and seborrhoeic dermatitis.

Another aspect of the invention relates to a composition containing, in a physiologically acceptable medium, at least one phylloseptin or dermaseptin antimicrobial peptide, a functional variant or a salt of such a peptide, and optionally at least one other active agent, which is active against desquamative disorders of the scalp and more particularly against dandruff and seborrhoeic dermatitis.

Another aspect of the invention relates to the use, in the manufacture of a pharmaceutical composition, of at least one phylloseptin or dermaseptin antimicrobial peptide, a functional variant or a salt of such a peptide, for combating desquamative disorders of the scalp and more particularly dandruff and seborrhoeic dermatitis.

The invention also relates to a cosmetic method for treating the hair and/or the scalp in order to treat desquamative disorders of the scalp and more particularly dandruff and seborrhoeic dermatitis, which consists in applying to the hair and/or the scalp at least one composition comprising, in a physiologically acceptable medium, at least one phylloseptin or dermaseptin antimicrobial peptide, a functional variant or a salt of such a peptide.

The term "physiologically acceptable medium" means a non-toxic medium that may be applied to the human scalp and human hair.

In the context of the present invention, the term "peptide" denotes a chain of amino acids linked together via a peptide bond (or amide bond).

The term "amino acids" denotes the following 20 amino acids in their laevorotatory (L) or dextrorotatory (D) form, preferably in their natural L form:

| Name | One-letter code | Three-letter code |
| --- | --- | --- |
| Alanine | A | Ala |
| Arginine | R | Arg |
| Asparagine | N | Asn |
| Aspartate | D | Asp |
| Cysteine | C | Cys |
| Glutamate | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophane | W | Trp |
| Tyrosine | Y | Tyr |
| Valine | V | Val |

The term "hydrophobic amino acid" denotes one of the following amino acids: I, L, V, M, F, Y, W, T, G, C or A. The term "alkaline hydrophilic amino acid" denotes one of the following amino acids: R, K or H. The term "neutral hydrophilic amino acid" denotes one of the following amino acids: S, P, N or Q. The term "acidic amino acid" denotes one of the following amino acids: D or E.

The term "antimicrobial peptide" denotes a peptide that prevents, inhibits or reduces the growth of a microorganism, or destroys such a microorganism. The term "microorganism" denotes a bacterium, a virus, a protozoon and/or a fungus. The peptides used according to the invention thus especially have antibacterial and/or antifungal activity, preferably activity against the microorganisms responsible for desquamative disorders of the scalp, and more particularly the microorganisms responsible for dandruff and seborrhoeic dermatitis. The antimicrobial activity of a peptide may be determined by measuring its "$IC_{50}$" or "inhibitory concentration 50", which corresponds to the concentration of a peptide that is necessary to reduce by 50% the in vitro growth of a population of microorganisms. In one particular embodiment of the invention, the antimicrobial peptides used have an $IC_{50}$ of between 10 ng/g and 100 mg/g of composition for combating the microorganisms responsible for desquamative disorders of the scalp, in particular for combating the microorganisms belonging to the genus *Malassezia* and its variants (in particular *M. ovalis, M. orbiculare, M. furfur, M. globosa* or *M. restricta*).

According to the invention, the antimicrobial peptide used is a peptide of natural or synthetic origin. According to one particular embodiment, the antimicrobial peptide comprises the sequence or consists of the sequence of a peptide secreted by the skin of animals, in particular terrestrial animals living in humid environments, such as forests, in particular by batrachians, more particularly those of the subfamily of Phyllomedusinae and the representatives of the six known genera: *Phyllomedusa* and in particular *Phyllomedusa hypochondrialis; Agalychnis; Pachymedusa; Phrynomedusa; Phasmahyla; Hylomanthis*. The invention also comprises the use of functional variants or of salts of such a peptide comprising the sequence of an antimicrobial peptide secreted by the skin of animals.

In one preferred embodiment, the antimicrobial peptide is selected from the group consisting of phylloseptin and dermaseptin peptides, described especially in Conceicao et al., *Peptides* 27 (2006), pp. 3092-3099.

The phylloseptin peptides used according to the invention may be described by formula (I) below:

$$\text{S-L-I-P-H-A-I-N-A-V-S-}X_1\text{-}X_2\text{-}X_3\text{-}X_4\text{-H-}X_5 \quad (I)$$

in which,
$X_1$ and $X_5$, independently, correspond to a hydrophobic or neutral hydrophilic amino acid;
$X_2$ and $X_3$, independently, correspond to a hydrophobic amino acid;
$X_4$ corresponds to an alkaline or neutral hydrophilic amino acid.

In one particular embodiment, the phylloseptin peptide used according to the invention is a peptide of formula (I'):

$$\text{F-L-S-L-I-P-H-A-I-N-A-V-S-}X_1\text{-}X_2\text{-}X_3\text{-}X_4\text{-H-}X_5 \quad (I').$$

In one particular embodiment, the peptide of the composition is a peptide of formula (I) or (I') in which $X_1$, $X_2$ and $X_3$ are hydrophobic amino acids, $X_4$ is an alkaline hydrophilic amino acid and $X_5$ is a neutral hydrophilic amino acid.

In another embodiment, the peptide of the composition is a peptide of formula (I) or (I') in which $X_1$ is a hydrophobic amino acid or a neutral hydrophilic amino acid, $X_2$, $X_3$ and $X_5$ are hydrophobic amino acids and $X_4$ is either an alkaline hydrophobic amino acid or a neutral hydrophilic amino acid.

In an alternative embodiment, the peptide of the composition is a peptide of formula (I) or (I') in which $X_1$, $X_2$, $X_3$ and $X_5$ are, independently, hydrophobic amino acids and $X_4$ corresponds to an alkaline hydrophilic amino acid.

According to one variant embodiment, the peptide of the composition is a peptide of formula (I) or (I') in which $X_1$ is selected from A and T, $X_2$ is selected from L and I, $X_3$ is selected from A and V, $X_4$ corresponds to K and $X_5$ corresponds to F in the implemented phylloseptin peptide of formula (I) or (I').

In one particular embodiment, the phylloseptin peptide used is a peptide of formula (I) or (I') amidated in its C-terminal position.

By way of illustration, the following peptides may be used according to the invention:

```
PS-1:  FLSLIPHAINAVSAIAKHN-NH2   (SEQ ID NO: 1)
PS-2:  FLSLIPHAINAVSTLVHHF-NH2   (SEQ ID NO: 2)
PS-3:  FLSLIPHAINAVSALANHG-NH2   (SEQ ID NO: 3)
PS-4:  FLSLIPHAINAVSTLVHHSG-NH2  (SEQ ID NO: 4)
PS-5:  FLSLIPHAINAVSAIAKHS-NH2   (SEQ ID NO: 5)
PS-6:  SLIPHAINAVSAIAKHF-NH2.    (SEQ ID NO: 6)
PS-7:  FLSLIPHAINAVSAIAKHF-NH2.  (SEQ ID NO: 7)
```

The peptides of sequences SEQ ID NO:1 to SEQ ID NO:7 are phylloseptin peptides present in batrachian secretions. Their use represents one particular embodiment of the invention. In one preferred embodiment, the invention relates to the use of the peptide PS-7 (SEQ ID NO:7).

The dermaseptin peptides used according to the invention may be described by formula (II) below:

$$X_a\text{-(L or M)-W-}X_b\text{-}X_c\text{-K-}X_d\text{-}X_e\text{-}X_f\text{-}X_g \quad (II)$$

in which:
$X_a$ denotes an apolar amino acid (F, G, I, L, V or A);
$X_b$ denotes a sequence of amino acids comprising two or three amino acids;
$X_c$ denotes an apolar amino acid (F, G, I, L, V or A);
$X_d$ denotes an amino acid or a sequence of two amino acids;
$X_e$ denotes an apolar amino acid (F, G, I, L, V or A) or K;
$X_f$ represents a set of two amino acids selected from the group consisting of GK, SK, AK, LK and GT;
$X_g$ represents a sequence of amino acids comprising between 10 and 25 amino acids;
and in which
$X_g$ comprises at least 50% of apolar amino acids (F, G, I, L, V or A) relative to the number of amino acids included in $X_g$;
more than 50% of the amino acids of the peptide are apolar amino acids (F, G, I, L, V or A);
the number of cationic residues (K, R or H) is less than or equal to 5;
the number of cationic residues (K, R or H) minus the number of anionic residues (D or E) is an integer between 0 and 3 inclusive.

Any combination of the following embodiments relating to the structure of the dermaseptin peptide may also be used in the invention:
$X_a$ is selected from A and G; and/or
$X_b$ denotes a sequence of two amino acids; and/or
$X_c$ is selected from 1 and L; and/or
$X_e$ is selected from the group consisting of A, I, L and V; and/or
$X_f$ represents GK; and/or
$X_g$ represents a sequence of amino acids comprising between 14 and 22 amino acids; and/or
$X_g$ comprises between 50% and 86% of apolar amino acids relative to the number of amino acids included in $X_g$; and/or
$X_g$ comprises at least 50% of apolar amino acids (F, G, I, L, V or A) of the entire peptide; and/or
the peptide comprises at least one amino acid selected from D and E.

According to one particular embodiment, the dermaseptin peptide amidated in the C-terminal position.

In one preferred embodiment, the dermaseptin peptide used is a peptide of formula (II) in which:

$X_a$ is selected from A and G;
$X_b$ is a sequence of two amino acids selected from the group consisting of SK and ST;
$X_c$ is selected from 1 and L;
$X_e$ is selected from the group consisting of A, I, L and V;
$X_f$ represents GK;
$X_g$ represents a sequence of amino acids comprising between 14 and 22 amino acids;
$X_3$ comprises between 50% and 86% of apolar amino acids, relative to the number of amino acids included in $X_g$;
$X_g$ comprises between 50% and 80% of apolar amino acids (F, G, I, L, V or A) of the entire peptide; and
the peptide comprises at least one amino acid selected from D and E.

In one particular embodiment, the dermaseptin peptide used is a peptide of formula (II')

$$X_a\text{-L-W-}X_b\text{-}X_c\text{-K-}X_d\text{-}X_e\text{-}X_f\text{-}X_g \qquad \text{(II')}$$

in which:

$X_a$ is selected from A and G;
$X_b$ corresponds to SK or ST, preferably ST;
$X_c$ is selected from 1 and L;
$X_e$ is selected from the group consisting of A, I, L and V;
$X_f$ represents GK;
$X_g$ represents a sequence of amino acids comprising 14 amino acids;
$X_g$ comprises 12 apolar amino acids; and
the peptide comprises at least one amino acid selected from D and E.

In one particular embodiment, the dermaseptin peptide used is selected from the group consisting of:

```
DS 01:
                              (SEQ ID NO: 8)
GLWSTIKQKGKEAAIAAAKAAGQAALGAL-NH2

DD L:
                              (SEQ ID NO: 9)
ALWKTLLKNVGKAAGKAALNAVTDMVNQ

DRS B1:
                              (SEQ ID NO: 10)
AMWKDVLKKIGTVALHAGKAALGAVADTISQ-NH2

DRS B5:
                              (SEQ ID NO: 11)
GLWNKIKEAASKAAGKAALGFVNEMV-NH2

(SEQ ID NO: 12)
DRS S1:
ALWKTMLKKLGTMALHAGKAALGAAADTISQGTQ,

DRS S2:
                              (SEQ ID NO: 13)
ALWFTMLKKLGTMALHAGKAALGAAANTISQGTQ,

DPh-1:
                              (SEQ ID NO: 14)
GLWSTIKNVGKEAAIAAGKAALGAL-NH2,
and Dermaseptin-L1:
                              (SEQ ID NO: 15)
GLWSKIKEAAKAAGKAALNAVTGLVNQGDQPS.
```

According to one particular embodiment, the dermaseptin peptide DPh-1 of sequence SEQ ID NO:14 is used.

The antimicrobial peptides used according to the present invention may be of natural origin or may be synthesized without difficulty by a person skilled in the art, using the conventional techniques of solid-phase or solution peptide synthesis (M. Bodanszky, Principles of Peptides Synthesis, 2nd ed., 1993, Edition Springer-Verlag). In one preferred embodiment, the antimicrobial peptides used according to the invention are synthetic peptides.

The antimicrobial peptides used according to the invention may also be produced by microorganisms, using bioengineering methods. In this case, it may be necessary to extract and purify the peptide from the producing microorganisms, before formulation. Alternatively, the producing microorganism may be applied directly to the site to be treated on the user, when the said microorganism is capable of excreting the produced antimicrobial peptide.

The use of functional variants of the phylloseptin and dermaseptin peptides is also envisaged. The term "functional variant" means a peptide derived from the sequence of a phylloseptin or dermaseptin peptide as described above, especially one of the peptides of sequence SEQ ID NO:1 to SEQ ID NO:15 described above, essentially comprising the same sequence, and having antimicrobial activity. Such a functional variant especially has a percentage of sequence identity of greater than 60% with the peptide from which it is derived, preferably greater than 70%, 80%, 90% and even more preferably greater than 95%. These functional variants may especially be designed by adding or deleting one or more amino acids at the ends of a peptide as described above, or in an internal part of its sequence. The functional variant may also be a peptide comprising one or more amino acid substitutions, especially conservative substitutions. A "conservative substitution" is a substitution of one amino acid residue by another that has similar chemical or physical properties (size, charge or polarity). By way of example, isoleucine, leucine, alanine, valine, phenylalanine, proline and glycine may be mutually conservatively substituted, as may lysine, histidine and arginine or serine, tyrosine and threonine or cysteine and methionine or asparagine, glutamine and tryptophan or aspartic acid and glutamic acid. The substitution may also correspond to the replacement of one or more L amino acids of the sequence with the corresponding D amino acids.

The preparation of functional variants is especially directed towards obtaining peptides whose properties have been improved. It may thus be sought to improve the selectivity of the antimicrobial peptides towards a particular microorganism responsible for a desquamative disorder of the scalp and in particular dandruff or seborrhoeic dermatitis and/or to increase its antimicrobial activity (making it possible, for example, to use such a modified peptide at a lower concentration). Such an improved peptide might allow the precise targeting of a specific microorganism such as a *Malassezia* yeast and its different variants (in particular *M. ovalis, orbiculare, furfur, globose* or *restricta*), while at the same time preserving the equilibrium of the beneficial microbial flora at the site of application of the peptide used according to the invention.

The antimicrobial activity of the peptides used according to the invention may be evaluated by measuring their minimum inhibitory concentration (MIC). Decreasing concentrations of peptides are contacted with standardised inoculum of microorganisms in a culture medium suitable for growth of said microorganisms in exponential growth phase. After incubation at the suitable temperature for the microorganism, the growth is evaluated by an OD (620 nm) measurement. Is considered as inhibitory, the product concentration that do not permit an optimal growth, compared to a control. The MIC obtained may be compared with the same measurement performed only with solvent (without the peptide) or with a compound of known antibiotic activity. This test may also be used to test the selectivity of the peptides used. This method can be used to determine the effect of the test peptide on a beneficial microorganism of the microbial flora of the scalp such as *Staphylococcus epidermidis*. Peptides that give on the strains responsible for desquamative disorders of the hair and/or the scalp (e.g., *M. furfur*) better inhibition than on the beneficial strains (e.g., *S. epidermidis*) will be selected.

In one particular embodiment, a functional variant of a phylloseptin or dermaseptin peptide is designed especially on the basis of one of the peptides of sequence SEQ ID NO:1 to 15, in particular SEQ ID NO:8 to 15 above, by:

- adding or deleting from one to five internal amino acids (i.e. amino acids that are not at the ends of the peptides described above). When the modification concerns more than one amino acid, the said addition or the said deletion may concern successive amino acids or amino acids that are separated in the sequence by one or more amino acids;
- the deletion of one to five amino acids at the ends of the peptide;
- the addition of one to 20 amino acids at one or both ends;
- the substitution of some of the natural amino acids of the sequence with natural or unnatural amino acids. This type of substitution may concern not more than a third and preferably not more than a quarter of the amino acids of the base sequence serving for the production of the modified peptide, and comprises conservative or non-conservative substitutions. Among the unnatural amino acids that may be used, mention may be made of 2-aminoheptanoic acid;
- modification of the N- and/or C-terminal end of the peptide by amidation, acylation or esterification;
- modification of the amino acid residues present in the peptide, especially by acetylation, methylation, acylation, esterification, etc., and
- any combination of the modifications described above.

These modifications may lead to increase or reduce the positive charge of the peptides (in order to improve the antimicrobial effect or in order potentially to improve the remanence and resistance of the product on the treated area), to give the peptides reactive functions that are useful in the context of the envisaged treatments, especially by adding functions that can act with thiols (in order to improve the resistance of the product on the treated area and/or to obtain wash resistance), to facilitate the removal or catabolism of the peptides and/or preventing the absorption of the peptides at the site of application, especially by adding ether oxide functions, polyol units (for example sugars) or hydrophobic functions such as fluoro or silicone functions, or yet to increase the lipophilicity and the compatibility with sebum (for treating greasier areas), in particular by branching a hydrocarbon chain onto the ends of the peptide or onto one or more amino acid residues.

In one preferred embodiment, the composition according to the invention comprises at least one antimicrobial peptide selected from the peptides PS-7 (SEQ ID NO:6) and DPh1 (SEQ ID NO:14).

According to one particular embodiment, the composition according to the invention comprises at least one antimicrobial peptide as defined above in a concentration of between 1 nM and 10 nM (i.e. between about 0.3 μg and about 3 μg per 100 g of composition).

According to the invention, the desquamative disorders of the hair and/or the scalp are, for example, dandruff or seborrhoeic dermatitis. Preferably, the said desquamative disorders of the scalp are those induced by the yeast of the genus *Malassezia* spp.

The compositions according to the invention may be intended for cosmetic or pharmaceutical use, particularly dermatological use. Preferably, the compositions according to the invention are intended for cosmetic use.

The compositions according to the invention are generally applied to the scalp or the hair.

According to the mode of administration, the composition of the invention may be in any galenic form normally used, particularly in cosmetology. A preferred composition of the invention is a cosmetic composition for topical application.

The composition according to the invention, after application to human hair and scalp, may be left in or rinsed out with water or with a shampoo. It may be in any form conventionally used in the field concerned, for example in the form of an aqueous or oily solution or of a dispersion of the lotion or serum type, emulsions of liquid or semi-liquid consistency of the milk type, obtained by dispersing a fatty phase in an aqueous phase (O/W) or conversely (W/O), or suspensions or emulsions of soft consistency of the aqueous or anhydrous cream or gel type, or alternatively microcapsules or microparticles, or vesicular dispersions of ionic and/or nonionic type. These compositions are prepared according to the usual methods.

The composition that may be used according to the invention may also be a haircare composition, and especially a shampoo, a hairsetting lotion, a medicated lotion, a styling cream or gel, a dye composition (especially for oxidation dyeing) optionally in the form of colouring shampoos, hair restructuring lotions, a permanent-waving composition (especially a composition for the first stage of a permanent-waving operation), a preparation (lotion, gel or shampoo) for combating hair loss, an antiparasitic shampoo, etc.

In one particular embodiment, the composition that may be used according to the invention is in the form of a rinse-out formulation. It may in particular correspond to a shampoo, a hair conditioner, a lotion, a gel or a foam. In addition to the ingredients conventionally used to produce them, these compositions may also comprise additives for increasing the deposition of the peptide during rinsing. Thus, the compositions may be prepared by combining these peptides with anionic polymers, amphoteric polymers, anionic polymer/cationic polymer or anionic polymer/amphoteric polymer combinations. It is also possible to combine these peptides with surfactants or mixtures of surfactants or surfactant/polymer mixtures to enhance the deposition at the time of rinsing.

In particular, mixtures of surfactants combining one or more anionic surfactants, in particular lauryl ether sulfate or lauryl sulfate, one or more amphoteric surfactants, such as those using betaine derivatives, and a nonionic surfactant, such as an APG, in particular in an embodiment in which the nonionic surfactant represents at least 20% by weight relative to the surfactants as a whole, are used.

The composition according to the invention may also be a leave-in formulation. Mention may be made especially in this respect of sprays, lacquers, mousses or lotions. The composition may also be formulated so as to allow a deposition of the peptide onto the scalp and to maintain a medium suitable for its efficacy (maintenance of water, glycols and glycerol at the surface of the scalp, for example). Examples that may be mentioned include emulsions and gels, forming a layer over the scalp and drying slowly (for example over several minutes, especially over 3 minutes). The composition according to the invention may also be formulated so as to allow the production of a temperature suited to the action of the peptides, after application to the scalp. These are self-heating products, which may act, for example, via exothermic reaction between two compounds. Examples that may be mentioned include compositions using a calcium salt such as calcium acetate or any other compound that shows a temperature increase on crystallization.

In one particular embodiment of the invention, a mask is applied to the scalp. This mask may be a preformed film, or a composition that forms after application of the film to the scalp (such as a composition that sets to a solid). With this formulation principle, the composition according to the invention may be applied in two or more stages. For example, a formulation containing the peptide is applied, and a gel or a mask is then applied.

The amounts of the various constituents of the compositions that may be used according to the invention are those conventionally used in the fields under consideration.

The compositions that may be used according to the invention may also consist of solid preparations constituting soaps or cleansing bars.

The compositions that may be used according to the invention may also be conditioned in the form of an aerosol composition also comprising a propellant under pressure.

According to another embodiment, the peptides as defined above are formulated by deposition onto particles or ligand-bound via anionic polymers. Naturally anionic particles, such as silicas, may be used. Cationic particles may also be used, such as alumina particles, which are surrounded with an anionic polymer such as an acrylate polymer or copolymer (typically with a ratio of polymer to particle of between 1% and 25% by weight).

According to another particular embodiment, the peptides as defined above are placed in a protective shell, for example a wax that melts on hairdrying at moderate temperature (for example between 40° C. and 50° C.). This shell protects the peptide while at the same time allowing its release when so desired.

The compositions according to the invention contain a physiologically acceptable medium. In particular, this medium contains an aqueous phase containing water and optionally at least one water-miscible organic solvent, for instance $C_2$ to $C_6$ monoalcohols such as ethanol, isopropanol or n-butanol, or polyols such as propylene glycol, glycerol or glycol ethers. This medium may contain an oily phase containing one or more water-immiscible fatty substances that are liquid at room temperature (25° C.) and atmospheric pressure, known as "oils".

The physiologically acceptable medium may also comprise at least one surfactant selected from nonionic surfactants, anionic surfactants, cationic surfactants and amphoteric surfactants, and mixtures thereof.

The compositions according to the invention may also contain as washing base at least one surfactant selected from anionic, nonionic and amphoteric surfactants, and mixtures thereof.

As anionic surfactants that may be used in the present invention, mention may be made especially of the salts, in particular the alkali metal salts such as the sodium salts, the ammonium salts, the amine salts, the amino alcohol salts or the alkaline-earth metal salts, for example the magnesium salts, of the following types: alkyl sulfates, alkyl ether sulfates, alkylamido ether sulfates, alkylarylpolyether sulfates, monoglyceride sulfates; alkylsulfonates, alkylamidesulfonates, alkylarylsulfonates, α-olefin sulfonates, paraffin sulfonates, alkylsulfosuccinates, alkyl ether sulfosuccinates, alkylamidesulfosuccinates, alkyl sulfoacetates, acylsarcosinates and acylglutamates, the alkyl and acyl groups of all these compounds comprising from 6 to 24 carbon atoms and the aryl group preferably denoting a phenyl or benzyl group, and mixtures thereof.

It is also possible to use as anionic surfactant monoesters of a $C_6$-$C_{24}$ alkyl and of polyglycoside dicarboxylic acids, such as alkyl glucoside citrates, alkyl polyglycoside tartrates and alkyl polyglycoside sulfosuccinates, alkyl sulfosuccinamates, acylisethionates and N-acyltaurates, the alkyl or acyl group of all these compounds comprising from 12 to 20 carbon atoms, and mixtures thereof.

Another group of anionic surfactants that may be used in the composition of the present invention is that of acyl lactylates, the acyl group of which comprises from 8 to 20 carbon atoms.

In addition, mention may also be made of alkyl-D-galactosideuronic acids and salts thereof and also polyoxyalkylenated ($C_6$-$C_{24}$)alkyl ether carboxylic acids, polyoxyalkylenated ($C_6$-$C_{24}$)alkyl($C_6$-$C_{24}$)aryl ether carboxylic acids, polyoxyalkylenated ($C_6$-$C_{24}$)alkylamido ether carboxylic acids and salts thereof, in particular those comprising from 2 to 50 ethylene oxide units, and mixtures thereof.

Alkyl sulfates, alkyl ether sulfates and alkyl ether carboxylates, and mixtures thereof, in particular in the form of alkali metal or alkaline-earth metal, ammonium, amine or amino alcohol salts are preferably used as anionic surfactant.

As amphoteric surfactant that may be used in the present invention, mention may be made of secondary or tertiary aliphatic amine derivatives, in which the aliphatic group is a linear or branched chain comprising from 8 to 22 carbon atoms and containing at least one anionic group, for instance a carboxylate, sulfonate, sulfate, phosphate or phosphonate group. Mention may be made in particular of ($C_8$-$C_{20}$)alkylbetaines, sulfobetaines, ($C_{8-20}$)alkylamido($C_6$-$C_8$)alkylbetaines and ($C_8$-$C_{20}$)alkylamido($C_6$-$C_8$)alkylsulfobetaines, and mixtures thereof.

Among the amine derivatives, mention may be made of the products sold under the name Miranol®, such as those described in U.S. Pat. No. 2,528,378 and U.S. Pat. No. 2,781,354 and classified in the CTFA dictionary, 3rd edition, 1982, under the names Amphocarboxyglycinate and Amphocarboxypropionate having the respective structures (2) and (3):

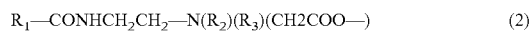

$$R_1\text{—CONHCH}_2\text{CH}_2\text{—N(R}_2)(R_3)(\text{CH2COO—}) \qquad (2)$$

in which:
$R_1$ represents an alkyl group derived from an acid Ra—COOH present in hydrolysed coconut oil, or a heptyl, nonyl or undecyl group,
$R_2$ represents a β-hydroxyethyl group, and
$R_3$ represents a carboxymethyl group; and

$$R_1'\text{—CONHCH}_2\text{CH}_2\text{—N(B)(C)} \qquad (3)$$

in which:
B represents —$CH_2CH_2OX'$,
C represents —$(CH_2)_z$—Y', with z=1 or 2,
X' represents the group —$CH_2CH_2$—COOH or a hydrogen atom,
Y' represents —COOH or the group —$CH_2$—CHOH—$SO_3H$,
$R_1'$ represents an alkyl group of an acid $R_1'$-COOH present in coconut oil or in hydrolysed linseed oil, an alkyl group, especially of $C_{17}$ and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoampho-dipropionic acid.

An example that may be mentioned is the cocoamphodiacetate sold by the company Rhodia under the trade name Miranol® C2M concentrate.

Among the amphoteric surfactants, (C8-20 alkyl)betaines, ($C_8$-$C_{20}$ alkyl)amido-($C_6$-$C_8$ alkyl)betaines and alkylamphodiacetates, and mixtures thereof, are preferably used.

As nonionic surfactants that may be used in the composition according to the invention, mention may be made of the known compounds described especially in the book "Handbook of Surfactants" by M. R. Porter, published by Blackie & Son (Glasgow and London), 1991, pp. 116-178). It is especially selected from polyethoxylated, polypropoxylated or polyglycerolated alcohols, α-diols, (C1-20)alkylphenols or fatty acids, with a fatty chain containing, for example, from 8 to 18 carbon atoms, the number of ethylene oxide or propylene oxide groups possibly ranging especially from 2 to 50 and the number of glycerol groups possibly ranging especially from 2 to 30, and mixtures thereof.

As nonionic surfactants that may be used in the invention, mention may also be made of condensates of ethylene oxide and of propylene oxide on fatty alcohols; polyethoxylated fatty amides preferably containing from 2 to 30 ethylene oxide units; polyglycerolated fatty amides comprising on average from 1 to 5 glycerol groups and in particular from 1.5 to 4 glycerol groups; ethoxylated fatty acid esters of sorbitan containing from 2 to 30 ethylene oxide units; fatty acid esters of sucrose; fatty acid esters of polyethylene glycol; ($C_6$-$C_{24}$ alkyl)polyglycosides; N—(C6-24 alkyl)glucamine derivatives; amine oxides such as ($C_{10}$-$C_{14}$ alkyl)amine oxides or N—($C_{10}$-$C_{14}$ acyl)aminopropylmorpholine oxides; mixtures thereof.

Among the nonionic surfactants mentioned above, ($C_6$-$C_{24}$ alkyl)polyglycosides are preferably used.

According to one particular embodiment of the invention, the washing base contains at least one anionic surfactant and at least one amphoteric or nonionic surfactant.

The total amount of surfactant is generally within the range from 0.01% to 50% by weight and preferably from 0.1% to 25% by weight relative to the total weight of the composition.

In particular, when the composition of the invention is in the form of a shampoo, the total amount of surfactants (or washing base) is selected in particular from 4% to 50% by weight, for example from 8% to 25% by weight, relative to the total weight of the cosmetic composition.

According to one particular embodiment, the composition according to the invention is a shampoo comprising at least one nonionic surfactant.

The composition according to the invention may also contain at least one additional ingredient conventionally used in the fields under consideration and selected from cosmetic active principles with a beneficial effect on the hair and/or the scalp, such as zinc salts of an organic acid (acetate, glycolate, lactate, gluconate or citrate) or of a mineral acid (chloride and sulfate), vitamins (E, C, B2, B5, F), UV-screening agents, radical scavengers, preserving agents, ceramides, plant extracts and formulation additives such as anionic, nonionic, cationic or amphoteric film-forming polymers, polymeric aqueous-phase or oily-phase thickeners, non-polymeric aqueous-phase thickeners such as hydroxylated or non-hydroxylated fatty acid amides or salts, nacreous agents, opacifiers, dyes that are soluble in the medium, pigments, fillers, fragrances, oils of mineral, plant and/or synthetic origin, esters of fatty acids and/or of fatty alcohols, waxes, pH stabilizers such as acids, bases or salts, organic solvents, silicones and electrolytes, and mixtures thereof.

The amounts of the various additional ingredients of the composition according to the invention are those generally used in the fields under consideration and are in particular within the range from 0.001% to 20% of the total weight of the composition. In addition, this composition is prepared according to the usual methods.

Advantageously, the pH of the composition of the present invention is selected in the range from 2 to 11 and preferentially from 3 to 10, for example from 5 to 8.

Advantageously, the composition according to the invention may also comprise a system reminding the user of the presence of the product on the scalp, or warning the user of the time when rinsing or drying should be performed, where appropriate (for example a dye or an odorous product).

Needless to say, a person skilled in the art will take care to select the optional additional ingredients and/or the amount thereof such that the advantageous properties of the composition according to the invention, namely the activity on desquamative disorders of the hair and/or the scalp, are not, or are not substantially, adversely affected by the envisaged addition.

According to yet another aspect, an object of the invention is a composition containing, in a physiologically acceptable medium, at least one peptide as described above and at least one other agent that is active against desquamative disorders of the scalp.

The other agents for combating desquamative disorders of the scalp are preferably selected from pyridinethione salts such as zinc pyrithione, 1-hydroxy-2-pyrrolidone derivatives such as piroctone and piroctone olamine; selenium sulfides such as selenium disulfide; climbazole, undecylenic acid; ketoconazole and cyclopirox, or mixtures thereof. Mention may also be made of natural products such as extracts (especially tea tree oil) and compounds such as salicylic acid. In practice, the additional active agent or the mixture of additional active agents may represent from 0.001% to 10% by weight and preferentially from 0.1% to 5% by weight relative to the total weight of the composition.

Other active agents for complementing or strengthen the action of the antimicrobial peptides may be used. Mention may be made in this respect of abrasive powders and active agents that can aid desquamation, such as mineral or metal powders (for example silica, alumina or corundum powder) or organic powders such as carbon black grains of different particle sizes. These abrasive active agents may be formulated in the composition according to the invention or may be used in the form of solid materials, for instance fabrics.

The composition according to the invention may also comprise active agents that aid in detaching squamae or in softening the bonds between microorganisms and the skin or the hair. Cationic surfactants, organic solvents such as alkyl acetates, acetone, silicones, plasticizers and thiols, for instance cysteine, may thus be used. It is also possible to use enzymes such as proteases, in particular keratinases or lipases. It is also possible to use protein-destructuring agents: urea and derivatives thereof, guanidine and salts thereof (hydroxides or carbonates), or ionic liquids, for example.

Advantageously, active agents that aid penetration may also be used, for instance hydrotropes, typically propylene carbonate, benzyl alcohol or benzoic acid.

According to another embodiment, the composition according to the invention also comprises another peptide or protein involved in defence of the skin, in particular a defensin (human β-defensin), human cathelicidin, alamethicin or a melittin.

The composition may also be prepared extemporaneously, immediately before use. A subject of the invention is then a cosmetic assembly for combating desquamative disorders of the scalp, comprising at least two compositions, one of the two compositions comprising at least one phylloseptin or dermaseptin antimicrobial peptide, or a variant of such a peptide, optionally in a physiologically acceptable medium. In this embodiment, mixing of the compositions must be performed beforehand by the user, or by a system that performs the mixing automatically. It may especially be envisaged to use a two-pocket system.

According to one embodiment, the cosmetic assembly is, for example, in the form of two parts to be mixed together at the time of use. The first composition contains the peptide and a solvent (water or aqueous mixture) with, for example, other ingredients such as preserving agents or thickeners. The second contains a mixture of surfactants and of care active agents, such as silicones or cationic polymers.

According to another embodiment, the first composition contains the peptide and a solvent (water or aqueous mixture) with, for example, other ingredients such as preserving agents or thickeners. The second contains an antifungal active agent such as selenium disulfide or zinc pyrithione, or a solvent or proteolytic compound. The first and/or second composition may contain surfactants and care active agents, such as silicones or cationic polymers.

According to another embodiment, the first composition contains the peptide and a solvent (water or aqueous mixture) with, for example, other ingredients such as preserving agents or thickeners. The second composition contains a probiotic agent. The first and/or second composition may contain surfactants and care active agents, such as silicones or cationic polymers.

A cosmetic assembly according to the invention may advantageously be used in a cosmetic scalp treatment method for combating desquamative disorders of the scalp, in which it is desired to stop the action of the peptide over time without intervention of the user after application of the antidandruff formulation. The assembly is then composed of a first composition containing at least one antimicrobial peptide as described above, and of a second composition, different from the first, containing a protease that is capable of inactivating the said at least one antimicrobial peptide. The cosmetic method according to the invention will then comprise the premixing of the two compositions of the cosmetic assembly according to the invention before applying the resulting mixture to the part to be treated. The action of the peptide will then be gradually stopped by digestion of the said peptide with the said protease.

According to yet another aspect, an object of the invention is a cosmetic scalp treatment method for combating desquamative disorders of the scalp, characterized in that a cosmetic composition comprising, in a physiologically acceptable medium, at least one antimicrobial peptide as described previously, a functional variant or a salt of such a peptide, is applied to the hair and/or the scalp.

An object of the invention is also a cosmetic method for treating the hair and/or the scalp to combat dandruff or seborrhoeic dermatitis, characterized in that a cosmetic composition comprising, in a physiologically acceptable medium, at least one antimicrobial peptide as described previously, a functional variant or a salt of such a peptide, is applied to the hair and/or the scalp.

The cosmetic treatment method according to the invention is particularly suitable when the said desquamative disorders of the scalp are induced by yeast of the genus *Malassezia* spp.

When the composition according to the invention is a rinse-out formulation, it is recommended to leave the composition to stand before rinsing and/or not to dry the hair too quickly after rinsing. A leave-on time of between 1 and 5 minutes may thus be envisaged.

In one particular embodiment, the method according to the invention is performed in two or more stages. A formulation containing the peptide is first applied and then, with or without intermediate rinsing, a formulation not containing the peptide (for example a shampoo or a hair conditioner) is applied. The order may be inverted.

The invention may allow the scalp to be treated periodically, for example once every two weeks, once a week or once every two or three days. The method according to the invention also comprises the daily application of the composition according to the invention, or even an application several times a day. The method according to the invention may also be performed according to the following modes: a first composition according to the invention is applied on the first day (for example containing 10 μM of peptide) and the scalp is then kept up with regular applications (for example once a day or once a week) by applying compositions containing small amounts of peptide (for example 1 μM of peptide).

The applications of the composition according to the invention may be alternated with more conventional treatments. Thus, it is possible to begin with application of a standard antidandruff product (based on piroctone olamine, zinc pyrithione, selenium disulfide or derivatives) and then to apply compositions based on peptide according to the invention. In this case, the application of the compositions according to the invention serves to control the growth of microorganisms responsible for desquamative disorders of the scalp, and thus to keep the scalp clean. The order of the applications may be inverted.

In one embodiment of the method according to the invention, the application of a standard composition for treating desquamative disorders of the scalp and of a composition according to the invention is alternated. Thus, a shampoo based on standard antidandruff active agent and a shampoo based on antimicrobial peptide according to the present invention may be applied, for example on the same day. The frequency of the treatments may be adapted. Thus, it may be envisaged to use a standard composition on one day, and then a composition according to the invention the following day, thus alternating the type of composition each day. According to another frequency, one of the compositions is used for one week, and the other composition is used the following week.

In another embodiment, the method according to the invention comprises the application of a composition according to the invention as described above, and then, after a leave-on time of between 1 and 15 minutes, the application of a second composition comprising a protease that is capable of inactivating the antimicrobial peptide present in the composition according to the invention. Thus, the user can stop the antimicrobial effect of the peptide when he considers the antidandruff effect obtained is sufficient. For example, the protease may be left to act for 1 to 15 minutes, if possible in humid or wet mode. Thus, the protease may be used in a lotion, shampoo, hair conditioner, etc. Alternatively, or in addition, the method according to the invention may comprise the inactivation of the antimicrobial peptide by heating the area treated with the composition according to the invention, for example using a hairdryer or heating tongs. The user who wishes to limit the antidandruff action only to the scalp can thus inhibit the action of the antimicrobial peptide. This embodiment is especially advantageous in the case of people with long hair. Specifically, these people may suffer from apprehension after applying an antidandruff product, associated with the fact that the active agent present on the hair may be transferred to the shoulders, the face or the eyes or may even be ingested if the person has the habit of putting their hair in their mouth. Localized inactivation of the peptide with an enzyme or by heat can overcome this problem. Other approaches may be used: application of a reductive, oxidative or denaturing solution, or application of a complexing composition. In one particular embodiment, the inactivating treatment is limited only to the ends of the hair (or only to the parts that may come into contact with the face and the shoulders). These same inactivating compounds may also be used to stop the action of the antimicrobial peptide over time, when the user considers that this action is sufficient or when he wishes to perform another treatment on his hair or scalp.

The invention is illustrated in greater detail in the examples that follow. These examples shall not in any way limit the scope of the invention.

EXAMPLES

Example 1

A synthetic DPh1 peptide is produced by chemical peptide synthesis according to the conventional methods well known to those skilled in the art.

The DPh1 peptide is introduced at a rate of 12 mg per 92 g of water, 4 g of isododecane and 4 g of APG (alkylpolyglucoside) nonionic surfactant.

The same formulation is prepared with PS7, at a rate of 18 mg instead of 12 mg.

The formulations are shaken at the time of use and applied to the root.

Example 2

Antimicrobial Activity of the Peptides According to the Invention on Microorganisms Responsible for Dandruff The test has been carried using a micromethod in microplates.

The tested peptide is contacted with an inoculum of microorganisms in a culture medium suitable for growth of said microorganisms (Sabouraud medium with 10% olive oil).

After incubation of the microplate from 24 to 48 hours at 32.5° C., optical density at 620 nm has been measured. Results are given as growth percent relative to a control without the peptide.

The peptides have been diluted in agar 1/1000 at a concentration of 0.1%, 0.25%, 0.5% and 1%. Each peptide concentration has been tested in triplicate. The test has been done twice.

Minimum inhibitory concentration (MIC) is defined as the first peptide concentration limiting significantly the microorganism growth, as compared to the control.

Results are shown in table 1 below:

| Microorganism | MIC | |
| --- | --- | --- |
| | PS-7 | DPh-1 |
| M. furfur | <0.1% | <0.1% |

These results show that peptides according to the invention are effective against the microorganisms model for dandruff.

Example 3

Examples of Formulations and Application a) Lotion

The phylloseptin peptide PS7 is produced by chemical peptide synthesis.

A composition is prepared, containing (per 100 g):
0.006 g of PS7
0.4 g of ammonium citrate
water qs 100 g After preparation, this composition is applied to the scalp, at a rate of 7 g to cover the head. It is then left to stand for 10 minutes, and then rinsed off.

b) Leave-On Gel

A composition is prepared, containing (per 100 g)
0.012 g of PS7
0.85 g of Jaguar HP 105 (hydroxypropyl guar; Rhodia)
water qs 100 g The gel is applied to the scalp (6 g per person). The operator applies the product so that it is crushed onto the scalp. The gel is left to dry. The product is not rinsed off.

c) Spray

A composition is prepared, containing (per 65 g)
0.020 g of PS7
1 g of AQ 38S (Polyester-5, Eastman Chemicals)
water qs 65 g This composition is placed in an aerosol can. The can is pressurized by introducing 35 g of dimethyl ether under pressure. The spray is applied to the scalp.

d) Lotion

The dermaseptin DPh1 is produced by chemical peptide synthesis.

A composition is prepared, containing (per 100 g):
0.01 g of DPh1
0.4 g of ammonium citrate
water qs 100 g After preparation, this composition is applied to the scalp, at a rate of 7 g to cover the head. Next, after drying, a second composition is applied in the form of a spray based on 5% of Mexomer in ethanol, pressurized with DME (65/35 proportion). The composition is then left to stand for 10 minutes.

e) Leave-On Gel

A composition is prepared, containing (per 100 g):
0.04 g of DPh1
0.85 g of Jaguar HP 105
water qs 100 g The gel is applied to the scalp (6 g per person). The operator applies the product such that it is crushed onto the scalp. It is rehydrated regularly with a water spray to prevent the gel from drying out.

f) Spray

A composition is prepared, containing (per 65 g)
0.010 g of PS7
0.010 g of DPh1
1 g of AQ 38S (Eastman Chemicals)
water qs 65 g This composition is placed in an aerosol can. The can is pressurized by introducing 35 g of dimethyl ether under pressure. The spray is applied to the scalp.

The invention claimed is:

1. A method for treating a desquamative disorder of the scalp, the method comprising applying at least one composition comprising a phylloseptin antimicrobial peptide, or a salt of said peptide, as antidandruff agent, to the hair, scalp, or both, of a person in need thereof, wherein the at least one composition comprises a phylloseptin peptide of formula (I'):

F-L-S-L-I-P-H-A-I-N-A-V-S-$X_1$-$X_2$-$X_3$-$X_4$-H-$X_5$    (I'), wherein:
$X_1$ and $X_5$, independently, represent a hydrophobic or neutral hydrophilic amino acid;
$X_2$ and $X_3$, independently, represent a hydrophobic amino acid; and
$X_4$ represents an alkaline or neutral hydrophilic amino acid,
wherein the phylloseptin antimicrobial peptide, or a salt of said peptide inhibits or reduces the growth of *Malassezia* yeast on the scalp.

2. The method of claim 1, wherein the at least one composition comprises a phylloseptin peptide of formula (I):

S-L-I-P-H-A-I-N-A-V-S-$X_1$-$X_2$-$X_3$-$X_4$-H-$X_5$    (I), wherein:
$X_1$ and $X_5$, independently, represent a hydrophobic or neutral hydrophilic amino acid;
$X_2$ and $X_3$, independently, represent a hydrophobic amino acid; and
$X_4$ represents an alkaline or neutral hydrophilic amino acid.

3. The method of claim 1, wherein the peptide is selected from the group consisting of:

| | | |
|---|---|---|
| PS-7: | FLSLIPHAINAVSAIAKHF-$NH_2$, | (SEQ ID NO: 7) |
| PS-1: | FLSLIPHAINAVSAIAKHN-$NH_2$, | (SEQ ID NO: 1) |
| PS-2: | FLSLIPHAINAVSTLVHHF-$NH_2$, | (SEQ ID NO: 2) |
| PS-3: | FLSLIPHAINAVSALANHG-$NH_2$, | (SEQ ID NO: 3) |
| PS-4: | FLSLIPHAINAVSTLVHHSG-$NH_2$, | (SEQ ID NO: 4) |
| PS-5: and | FLSLIPHAINAVSAIAKHS-$NH_2$, | (SEQ ID NO: 5) |
| PS-6: | SLIPHAINAVSAIAKHF-$NH_2$. | (SEQ ID NO: 6) |

4. The method of claim 1, wherein the desquamative disorder is dandruff or seborrhoeic dermatitis.

5. The method of claim 1, wherein:
the desquamative disorder is dandruff; and
the method comprises topical application of a composition comprising a phylloseptin peptide to the scalp of a person in need thereof.

6. The method of claim 1, wherein said peptide is PS-7 (SEQ ID NO: 7) or DPh-1 (SEQ ID NO: 14).

7. The method of claim 1, wherein the at least one composition is in the form of a shampoo.

8. The method of claim 1, wherein the at least one composition further comprises another active agent for treating desquamative disorders of the skin.

9. The method of claim 8, wherein the at least one composition further comprises piroactone olamine.

* * * * *

```
                        SEQUENCE LISTING

<160> NUMBER OF SEQ ID NOS: 15

<210> SEQ ID NO 1
<211> LENGTH: 19
<212> TYPE: PRT
<213> ORGANISM: Phyllomedusa hypochondrialis
<220> FEATURE:
<221> NAME/KEY: MISC_FEATURE
<222> LOCATION: (19)..(19)
<223> OTHER INFORMATION: amidated C-terminal end

<400> SEQUENCE: 1

Phe Leu Ser Leu Ile Pro His Ala Ile Asn Ala Val Ser Ala Ile Ala
1               5                   10                  15

Lys His Asn

<210> SEQ ID NO 2
<211> LENGTH: 19
<212> TYPE: PRT
<213> ORGANISM: Phyllomedusa Hypochondrialis
<220> FEATURE:
<221> NAME/KEY: MISC_FEATURE
<222> LOCATION: (19)..(19)
<223> OTHER INFORMATION: amidated C-terminal end

<400> SEQUENCE: 2

Phe Leu Ser Leu Ile Pro His Ala Ile Asn Ala Val Ser Thr Leu Val
1               5                   10                  15

His His Phe

<210> SEQ ID NO 3
<211> LENGTH: 19
<212> TYPE: PRT
<213> ORGANISM: Phyllomedusa Hypochondrialis
<220> FEATURE:
<221> NAME/KEY: MISC_FEATURE
<222> LOCATION: (19)..(19)
<223> OTHER INFORMATION: amidated C-terminal end

<400> SEQUENCE: 3

Phe Leu Ser Leu Ile Pro His Ala Ile Asn Ala Val Ser Ala Leu Ala
1               5                   10                  15

Asn His Gly

<210> SEQ ID NO 4
<211> LENGTH: 20
<212> TYPE: PRT
<213> ORGANISM: Phyllomedusa oreades
<220> FEATURE:
<221> NAME/KEY: MISC_FEATURE
<222> LOCATION: (20)..(20)
<223> OTHER INFORMATION: amidated C-terminal end

<400> SEQUENCE: 4

Phe Leu Ser Leu Ile Pro His Ala Ile Asn Ala Val Ser Thr Leu Val
```

```
1               5                   10                  15
His His Ser Gly
            20

<210> SEQ ID NO 5
<211> LENGTH: 19
<212> TYPE: PRT
<213> ORGANISM: Phyllomedusa oreades
<220> FEATURE:
<221> NAME/KEY: MISC_FEATURE
<222> LOCATION: (19)..(19)
<223> OTHER INFORMATION: amidated C-terminal end

<400> SEQUENCE: 5

Phe Leu Ser Leu Ile Pro His Ala Ile Asn Ala Val Ser Ala Ile Ala
1               5                   10                  15

Lys His Ser

<210> SEQ ID NO 6
<211> LENGTH: 17
<212> TYPE: PRT
<213> ORGANISM: Phyllomedusa hypochondrialis
<220> FEATURE:
<221> NAME/KEY: MISC_FEATURE
<222> LOCATION: (17)..(17)
<223> OTHER INFORMATION: amidated C-terminal end

<400> SEQUENCE: 6

Ser Leu Ile Pro His Ala Ile Asn Ala Val Ser Ala Ile Ala Lys His
1               5                   10                  15

Phe

<210> SEQ ID NO 7
<211> LENGTH: 19
<212> TYPE: PRT
<213> ORGANISM: Phyllomedusa azurea
<220> FEATURE:
<221> NAME/KEY: MISC_FEATURE
<222> LOCATION: (19)..(19)
<223> OTHER INFORMATION: amidated C-terminal end

<400> SEQUENCE: 7

Phe Leu Ser Leu Ile Pro His Ala Ile Asn Ala Val Ser Ala Ile Ala
1               5                   10                  15

Lys His Phe

<210> SEQ ID NO 8
<211> LENGTH: 29
<212> TYPE: PRT
<213> ORGANISM: Phyllomedusa oreades
<220> FEATURE:
<221> NAME/KEY: MISC_FEATURE
<222> LOCATION: (29)..(29)
<223> OTHER INFORMATION: amidated C-terminal end

<400> SEQUENCE: 8

Gly Leu Trp Ser Thr Ile Lys Gln Lys Gly Lys Glu Ala Ala Ile Ala
1               5                   10                  15

Ala Ala Lys Ala Ala Gly Gln Ala Ala Leu Gly Ala Leu
            20                  25

<210> SEQ ID NO 9
<211> LENGTH: 28
<212> TYPE: PRT
<213> ORGANISM: Phyllomedusa distincta
```

<400> SEQUENCE: 9

Ala Leu Trp Lys Thr Leu Leu Lys Asn Val Gly Lys Ala Ala Gly Lys
1               5                   10                  15

Ala Ala Leu Asn Ala Val Thr Asp Met Val Asn Gln
            20                  25

<210> SEQ ID NO 10
<211> LENGTH: 31
<212> TYPE: PRT
<213> ORGANISM: Phyllomedusa bicolor
<220> FEATURE:
<221> NAME/KEY: MISC_FEATURE
<222> LOCATION: (31)..(31)
<223> OTHER INFORMATION: amidated C-terminal end

<400> SEQUENCE: 10

Ala Met Trp Lys Asp Val Leu Lys Lys Ile Gly Thr Val Ala Leu His
1               5                   10                  15

Ala Gly Lys Ala Ala Leu Gly Ala Val Ala Asp Thr Ile Ser Gln
            20                  25                  30

<210> SEQ ID NO 11
<211> LENGTH: 26
<212> TYPE: PRT
<213> ORGANISM: Phyllomedusa bicolor
<220> FEATURE:
<221> NAME/KEY: MISC_FEATURE
<222> LOCATION: (26)..(26)
<223> OTHER INFORMATION: amidated C-terminal end

<400> SEQUENCE: 11

Gly Leu Trp Asn Lys Ile Lys Glu Ala Ala Ser Lys Ala Ala Gly Lys
1               5                   10                  15

Ala Ala Leu Gly Phe Val Asn Glu Met Val
            20                  25

<210> SEQ ID NO 12
<211> LENGTH: 34
<212> TYPE: PRT
<213> ORGANISM: Phyllomedusa sauvagii

<400> SEQUENCE: 12

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 13
<211> LENGTH: 34
<212> TYPE: PRT
<213> ORGANISM: Phyllomedusa sauvagii

<400> SEQUENCE: 13

Ala Leu Trp Phe Thr Met Leu Lys Lys Leu Gly Thr Met Ala Leu His
1               5                   10                  15

Ala Gly Lys Ala Ala Leu Gly Ala Ala Ala Asn Thr Ile Ser Gln Gly
            20                  25                  30

Thr Gln

<210> SEQ ID NO 14

```
<211> LENGTH: 25
<212> TYPE: PRT
<213> ORGANISM: Phyllomedusa hypochondrialis
<220> FEATURE:
<221> NAME/KEY: MISC_FEATURE
<222> LOCATION: (25)..(25)
<223> OTHER INFORMATION: amidated C-terminal end

<400> SEQUENCE: 14

Gly Leu Trp Ser Thr Ile Lys Asn Val Gly Lys Glu Ala Ala Ile Ala
1               5                   10                  15

Ala Gly Lys Ala Ala Leu Gly Ala Leu
            20                  25

<210> SEQ ID NO 15
<211> LENGTH: 32
<212> TYPE: PRT
<213> ORGANISM: Hylomantis lemur

<400> SEQUENCE: 15

Gly Leu Trp Ser Lys Ile Lys Glu Ala Ala Lys Ala Ala Gly Lys Ala
1               5                   10                  15

Ala Leu Asn Ala Val Thr Gly Leu Val Asn Gln Gly Asp Gln Pro Ser
            20                  25                  30
```